United States Patent [19]
Drabek

[11] 3,973,014
[45] Aug. 3, 1976

[54] THIOLPHOSPHORIC ACID ESTER INSECTICIDE

[75] Inventor: Jozef Drabek, Allschwil, Switzerland

[73] Assignee: Ciba-Geigy Corporation, Ardsley, N.Y.

[22] Filed: May 2, 1975

[21] Appl. No.: 574,197

Related U.S. Application Data

[62] Division of Ser. No. 426,777, Dec. 20, 1973, Pat. No. 3,896,191.

[30] Foreign Application Priority Data

Dec. 22, 1972 Switzerland.................... 18732/72

[52] U.S. Cl. ............................................. 424/225
[51] Int. Cl.² ............................................ A01N 9/36
[58] Field of Search ................................... 424/225

[56] References Cited
UNITED STATES PATENTS 3,839,511  10/1974  Kishino et al. ..................... 260/964

FOREIGN PATENTS OR APPLICATIONS 1,567,444  5/1969  France

Primary Examiner—Albert T. Meyers
Assistant Examiner—Allen J. Robinson
Attorney, Agent, or Firm—Harry Falber; Frederick H. Rabin

[57] ABSTRACT

Insecticidal and acaricidal composition and method utilizing the phosphoric acid ester of the formula

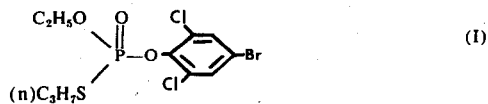

2 Claims, No Drawings

THIOLPHOSPHORIC ACID ESTER INSECTICIDE
This is a divisional of application Ser. No. 426,777 filed on Dec. 20, 1973, now U.S. Pat. No. 3,896,191.
The present invention relates to the thiolphosphoric acid ester of the formula
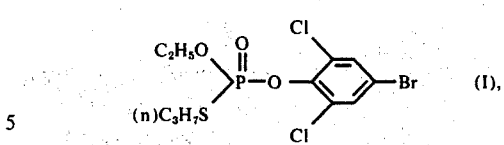
to processes for the preparation thereof, and to its application in pest control.
The compound of formula I can be prepared by the following processes:
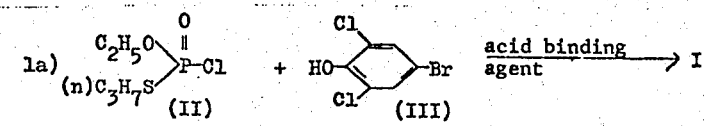
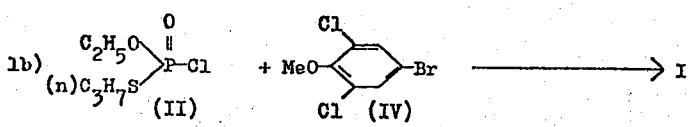
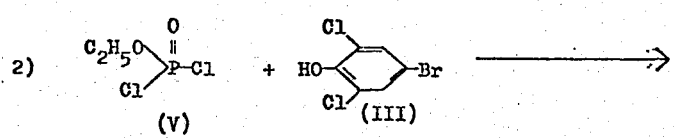
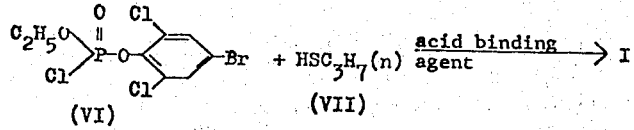
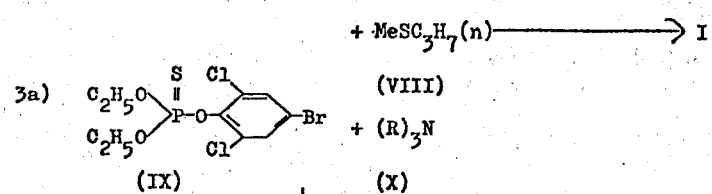
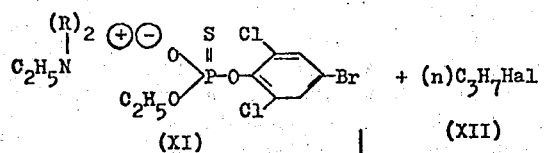

3b) 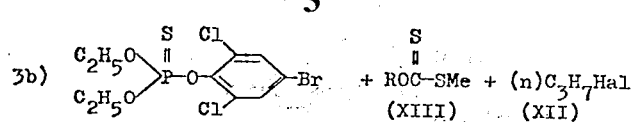

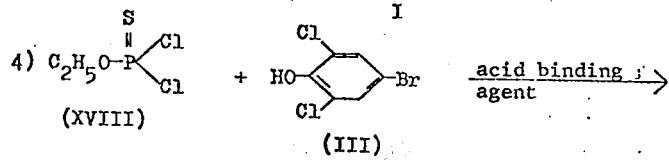

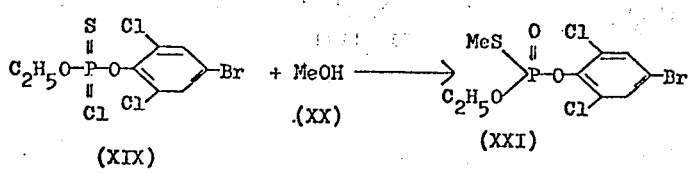

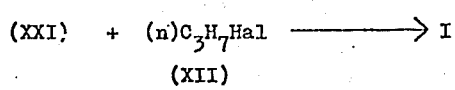

In the formulae IV, VII, VIII, X, XI, XIII, XIV, XV, XVI, XVII and XX, Me stands for an alkali metal, especially for sodium or potassium, ammonium or alkylammonium; R stands for $C_1$ $C_4$—alkyl such as methyl or ethyl; and Hal for chlorine, bromine or iodine.

Suitable acid binding agents are: tertiary amines, e.g. trialkylamines, pyridine, dialkylanilines; inorganic bases such as hydrides or hydroxides; carbonates and bicarbonates of alkali metals and alkaline-earth metals. Sometimes it is necessary in the reactions to use catalysts such as, e.g. copper or copper chloride. The processes 1a and 1b, 2, 3 and 3b and 4 are performed at a reaction temperature of between 0° and 130°C, under normal pressure and in solvents or diluents inert to the reactants.

Inert solvents or diluents which are suitable are, e.g. ethers ethereal compounds such as diethyl ether, dipropyl ether, dioxane or tetrahydrofuran; amides such as N,N-dialkylated carboxylic acid amides; aliphatic, aromatic as well as halogenated hydrocarbons, particularly benzene, toluene, xylenes, chloroform or chlorobenzene; nitriles such as acetonitrile; or dimethylsulphoride. Also alcohols and water are suitable in the case of processes 3a and 3b.

The starting materials of formula II can be produced by methods analogous to known methods, e.g. by those described in J. Org. Chem. 30,3217 (1965).

Compared with analogous compounds from the Swiss Patent Specification No. 500,230 and from the German 'Offenlegungsschrift' No. 2,163,391, the compound of formula I has a surprisingly better insecticidal and acaricidal action, particularly against Heliothis virescens larvae and Chilo suppressalis larvae, and a toxicity suitable for application. The action of the compounds according to the invention extends, in addition, to all development stages, such as, e.g. eggs, larvae, nymphs, pupae and adults of insects of the families: Acrididae, Blattidae, Gryllidae, Gryllotalpidae, Tettigoniidae, Cimicidae, Phyrrhocoridae, Reduviidae, Aphididae, Delphacidae, Diaspididae, Pseudococcidae, Chrysomelidae, Coccinellidae, Bruchidae, Scarabaeidae, Dermestidae, Tenebrionidae, Curculionidae, Tineidae, Noctuidae, Lymantriidae, Pyralidae, Galleridae, Culicidae, Tipulidae, Stomoxydae, Muscidae, Calliphoridae, Trypetidae, Pulicidae, as well as acarids of the families: Ixodidae, Argasidae, Tetranychidae, Dermanyssidae.

The insecticidal or acaricidal action can be appreciably broadened and adapted to suit the given circumstances by the addition of other insecticides and/or acaricides. Suitable additives are, for example:
organic phosphorus compounds,
nitrophenols and derivatives,
formamidines,
carbamates and
chlorinated hydrocarbons.

The agents according to the invention are prepared in a known manner by the intimate mixing and/or grinding of the active substance of formula I with suitable carriers, optionally with the addition of dispersing agents or solvents which are inert to the active substances. The active substances can be obtained and used in the following forms:

solid preparations: dusts, scattering agents, granulates, coated granulates, impregnated granulates, and homogeneous granulates;

liquid preparations:
a. water-dispersible active-substance concentrates: wettable powders, pastes or emulsions;
b. solutions.

The content of active substance in the described agents is between 0.1 and 95%; it is to be mentioned in this connection that in the case of application from an aeroplane, or by means of other suitable devices, concentrations of up to 99.5% can be employed, or even the pure active substance.

The active substance of formula I can be prepared, for example, as follows:

Dusts:

The following substances are used in the preparation of (a) a 5% dust, and (b) a 2% dust:

(a)

5 parts of active substance,
95 parts of talcum;

(b)

2 parts of active substance,
1 part of highly dispersed silicic acid,
97 parts of talcum.

The active substances are mixed and ground with the carriers.

Granulate:

The following substances are used to produce a 5% granulate:

5 parts of active substance,
0.25 parts of epichlorhydrin,
0.25 parts of cetyl polyglycol ether,
3.50 parts of polyethylene glycol,
91 parts of kaolin (particle size 0.3 - 0.8 mm).

The active substance is mixed with epichlorhydrin and dissolved with 6 parts of acetone; the polyethylene glycol and cetyl polyglycol ether are then added. The solution thus obtained is sprayed on to kaolin, and the acetone subsequently evaporated off in vacuo.

Wettable powder:

The following constituents are used for the preparation of (a) a 40%, (b) and (c) a 25%, and (d) a 10% wettable powder:

(a)

40 parts of active substance,
5 parts of sodium lignin sulphonate,
1 part of sodium dibutyl-naphthalene sulphonate,
54 parts of silicic acid.

(b)

25 parts of active substance,
4.5 parts of calcium lignin sulphonate
1.9 parts of Champagne chalk/hydroxyethyl cellulose mixture (1:1),
1.5 parts of sodium dibutyl naphthalene sulphonate,
19.5 parts of silicic acid,
19.5 parts of Champagne chalk,
28.1 parts of kaolin.

(c)

25 parts of active substance,
2.5 parts of isooctylphenoxy-polyoxyethylene-ethanol,
1.7 parts of Champagne chalk/hydroxyethyl cellulose mixture (1:1),
8.3 parts of sodium aluminum silicate,
16.5 parts of kieselguhr,
46 parts of kaolin.

(d)

10 parts of active substance,
3 parts of a mixture of the sodium salts of saturated fatty alcohol sulphates,
5 parts of napthalenesulphonic acid/formaldehyde condensate,
82 parts of kaolin.

The active substance is intimately mixed, in suitable mixers, with the additives, and the mixture then ground in the appropriate mills and rollers. Wettable powders are obtained which can be diluted with water to give suspensions of any desired concentrations.

Emulsifiable concentrates:

The following substances are used to produce (a) a 10% and (b) a 25% emulsifiable concentrate:

(a)

10 parts of active substance,
3.4 parts of epoxidised vegetable oil,
13.4 parts of a combination emulsifier consisting of fatty alcohol polyglycol ether and alkylarylsulphonate calcium salt,
40 parts of dimethylformamide,
43.2 parts of xylene.

(b) 25 parts of active substance, 2.5 parts of epoxidised vegetable oil,
10 parts of an alkylarylsulphonate/fatty alcohol-polyglycol ether mixture
5 parts of dimethylformamide,
57.5 parts of xylene.

From these concentrates it is possible to produce, by dilution with water, emulsions of any desired concentration.

Spray:

The following constituents are used to prepare a 5% spray:

5 parts of active substance,
1 part of epichlorhydrin,
94 parts of ligroin (boiling limits 160°-190°C).

EXAMPLE 1

Preparation of the compound of the formula

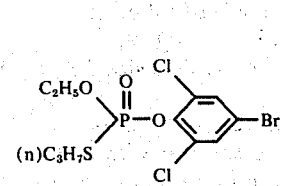

An amount of 35.2 of 2,6-dichloro-4-bromophenol is dissolved in 150 ml of benzene, and 15.1 g of triethylamine then added. While continuous stirring is maintained, an addition is made dropwise at 10° – 15°C of 32.0 g of O-ethyl-S-(n)-propylchlorothiophosphate. Stirring is afterwards continued for 12 hours at room temperature. The mixture is subsequently washed with water, 3% $Na_2CO_3$-solution, and again with water; it is then dried over anhydrous sodium sulphate. The benzene is distilled off, and the residue purified by molecular distillation (boiling temperature 150°C/0.001 Torr).

The ester of the above given formula is obtained having a refractive index of $n_D^{20} = 1.5576$.

Analysis: for $C_{11} H_{14} Br Cl O_3 P S$

| Calculated: | Found: |
|---|---|
| % P 7.9 | 7.7 |
| % Br 19.6 | 19.5 |

EXAMPLE 2

Comparative tests
Active substances

A 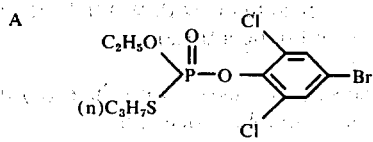 according to the invention

B 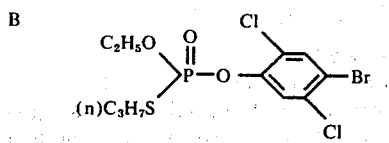 known from DOS 2,163,391

C 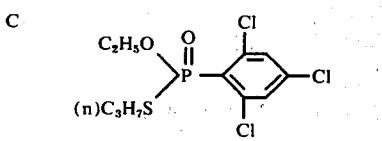 known from DOS 2,163,391 and from S.P. 500,230

Test insects
  Heliothis virescense larvae,
  Chilo suppressalis larvae,
  Aëdes aegypti larvae,
  Ripicelphalus bursa (adults and larvae).
Test emulsion
  10 parts of active substance,
  3.4 parts of epoxidised vegetable oil,
  3.4 parts of a combination emulsifier consisting of tetraalcohol polyglycol ether and alkylarylsulphonate calcium salt,
  40 parts of dimethylformamide,
  43.2 parts of xylene.
Test granulate
  5 parts of active substance,
  0.25 parts of epichlorohydrin,
  0.25 parts of ethyl polyglycol ether,
  3.5 parts of polyethylene glycol,
  91.0 parts of kaolin (particle size 0.3 to 0.8 mm).
Tests and results
  a. Insecticidal stomach poison action
  Cotton plants were sprayed with a 0.05% aqueous active-substance emulsion (obtained from a 10% emulsifiable concentrate).

Eight days after drying of the coating, Heliothis virescens larvae $L_3$ were placed on the cotton plants. The test was carried out 24°C with 60% relative humidity and the initial effect estimated as percentages.

Result

| % destroyed after 8 days with 500 ppm of active substance | | Toxicity $LD_{50}$ rat orally (mg/kg) |
|---|---|---|
| A | 90% | 800 |
| B | 0% | 320 |
| C | 20% | 150 | b. Action against Chilo suppressalis
Rice plants of the variety Caloro were planted, 6 plants per pot, in plastic pots having a top diameter of 17 cm, and grown to a height of ca. 60 cm. Infestation with Chilo suppressalis larvae ($L_1$; 3–4 mm long) was carried out 2 days after application of the active substance in granular form (amount applied = 8 kg of active substance per hectare) to the paddy water. The assessment of the insecticidal action was made 10 days after application of the granulate.

Result
% destroyed after 10 days with 400 ppm
| A | 100% |
| B | 0% |
| C | 0% | c. Action against ticks Rhipicephalus bursa
In each case 5 adult ticks or 50 tick larvae were placed into a small glass test tube, and the test tubes then immersed for 1 to 2 minutes in 2 ml of an aqueous emulsion from a dilution series of 100, 10, 1 and 0.1 ppm of test substance. The tubes were then sealed with a standardised cotton plug, and inverted so that the active substance emulsion could be absorbed by the cotton wool.

An evaluation was made in the case of the adults after 2 weeks, and in the case of the larvae after 2 days. There were two repeats for each test.

Result
| Active substance | 100% action with X ppm against Rhipicephalus bursa | |
|---|---|---|
| | Adults | Larvae |
| A | 0.1 | 0.1 |
| B | 5 | 0.1 |
| C | 1 | 1 | d. Action against mosquito larvae (Aëdes aegypti)
An amount of 1 ml of an acetone solution of the test substances was transferred by pipet into 100 ml of water in a beaker, so that the concentration was 1 ppm or 0.1 ppm.

Eight days after the treatment, 4-day-old Aëdes aegypti larvae were applied and the destruction of the insects estimated in percent.

Result
| Active substance | Concentration (ppm) | % Destroyed after 8 days |
|---|---|---|
| A | 1 | 100 |
|   | 0.1 | 100 |
| B | 1 | 0 |
|   | 0.1 | 0 |
| C | 1 | 100 |

| Result Active substance | Concentration (ppm) | % Destroyed after 8 days |
|---|---|---|
| | 0.1 | 0 |

Findings

While compound A in Tests (a) to (d) has an almost 100% action against *Heliothis virescens* and *Chilo suppressalis* larvae, adults and larvae of *Rhipicephalus bursa* and mosquito larvae, compounds B and C are insufficiently effective or ineffective in the tested concentrations.

What we claim is:

1. An insecticidal or acaricidal composition comprising an insecticidally or acaricidally effective amount of

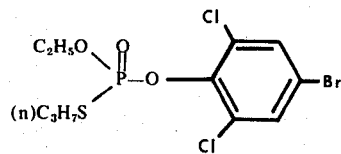

together with a suitable carrier therefor.

2. A method for combatting insects or acarids which comprises applying to the loci thereof an insecticidally or acaricidally effective amount of

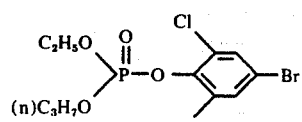

* * * * *

UNITED STATES PATENT AND TRADEMARK OFFICE
CERTIFICATE OF CORRECTION

PATENT NO. : 3,973,014
DATED : August 3, 1976
INVENTOR(S) : Jozef Drabek

It is certified that error appears in the above–identified patent and that said Letters Patent are hereby corrected as shown below:

In the claims, Claim 2, Column 10, Line 15, the formula should appear as follows:

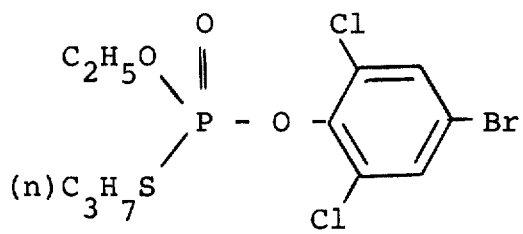

Signed and Sealed this

First Day of March 1977

[SEAL]

Attest:

RUTH C. MASON
*Attesting Officer*

C. MARSHALL DANN
*Commissioner of Patents and Trademarks*